US012740931B2

(12) United States Patent
Mondon et al.

(10) Patent No.: US 12,740,931 B2
(45) Date of Patent: Sep. 22, 2026

(54) COSMETIC OR DERMATOLOGICAL COMPOSITION ACTING IN PARTICULAR ON THE EFFECTS OF BLUE LIGHT ON SKIN AND ITS APPENDAGES, AND ASSOCIATED USES

(71) Applicant: Sederma, Le Perray-en-Yvelines (FR)

(72) Inventors: Philippe Mondon, Le Perray-en-Yvelines (FR); Thibault Marchand, Le Perray-en-Yvelines (FR); Sandra Brahimi, Le Perray-en-Yvelines (FR); Emmanuel Doridot, Le Perray-en-Yvelines (FR)

(73) Assignee: Sederma, Le Perray-en-Yvelines (FR)

( * ) Notice: Subject to any disclaimer, the term of this patent is extended or adjusted under 35 U.S.C. 154(b) by 1030 days.

(21) Appl. No.: 17/785,555

(22) PCT Filed: Dec. 14, 2020

(86) PCT No.: PCT/EP2020/086037

§ 371 (c)(1),
(2) Date: Jun. 15, 2022

(87) PCT Pub. No.: WO2021/122482

PCT Pub. Date: Jun. 24, 2021

(65) Prior Publication Data

US 2023/0026167 A1 Jan. 26, 2023

(30) Foreign Application Priority Data

Dec. 20, 2019 (FR) ....................................... 1915141

(51) Int. Cl.

| | |
|---|---|
| ***A61K 8/64*** | (2006.01) |
| ***A61K 8/37*** | (2006.01) |
| ***A61K 8/49*** | (2006.01) |
| ***A61Q 17/04*** | (2006.01) |
| ***A61Q 19/08*** | (2006.01) |

(52) U.S. Cl.

CPC ................ *A61K 8/64* (2013.01); *A61K 8/375* (2013.01); *A61K 8/498* (2013.01); *A61Q 17/04* (2013.01); *A61Q 19/08* (2013.01); *A61K 2800/522* (2013.01)

(58) Field of Classification Search

None

See application file for complete search history.

(56) References Cited

U.S. PATENT DOCUMENTS

| | | | |
|---|---|---|---|
| 2011/0028095 | A1 * | 2/2011 | Reznik et al. |
| 2021/0052480 | A1 | 2/2021 | Mondon et al. |

FOREIGN PATENT DOCUMENTS

| | | | | | |
|---|---|---|---|---|---|
| WO | 2005102266 | A1 | 11/2005 | | |
| WO | WO-2012143845 | A2 * | 10/2012 | ............ | A61K 38/06 |
| WO | 2014080376 | A2 | 5/2014 | | |
| WO | 2015181688 | A1 | 12/2015 | | |
| WO | 2016097965 | A1 | 6/2016 | | |
| WO | 2017216177 | A1 | 12/2017 | | |
| WO | 2018162368 | A1 | 9/2018 | | |

OTHER PUBLICATIONS

Database GNPD [Online] Mintel; May 25, 2006, 3 pages, Anonymous: "Anti-Aging Lifting Treatment Mask", XP055715639, retrieved from www.gnpd.com, Database Accession No. 536413.
Greentech Presentation, Feb. 1, 2017, 63 pages, XP055715679, Retrieved from the Internet: https://www.kalekimya.com/admin/hizmetler_dokuman/1502787476_2017-02_GREENTECH_Trends.pdf [retrieved on Jul. 16, 2020].
Solabia Group, "Blueshield ® [Blue Light pollution Defender]", Sep. 17, 2018, 4 pages, XP055715690, https://www.cosmeticsdesign-asia.com/Product-innovations/BLUESHIELD-R-To-protect -skin-from-digital-pollution-induced-aging [Retrieved on Jul. 16, 2020].
International Search Report and Written Opinion for International Application No. PCT/EP2020/086037, dated Mar. 12, 2021, 11 pages.

* cited by examiner

*Primary Examiner* — David J Blanchard
*Assistant Examiner* — Sarah J Chickos
(74) *Attorney, Agent, or Firm* — Buchanan Ingersoll & Rooney PC

(57) ABSTRACT

A composition is described, comprising or consisting of chrysin, rosmarinic acid, at least one peptide or derivative thereof, having a sequence of 4 to 10 amino acids comprising the active sequence GQPR and a physiologically acceptable medium. A derivative corresponds to the active sequence GQPR modified at the N-terminal end with an acyl (—CO—$R^1$), sulfonyl (—$SO_2$-$R^1$) group or a biotinoyl group and/or at the C-terminal end with an $OR^1$, $NH_2$, $NHR^1$ group or $NR^1R^2$, $R^1$ and $R^2$ being as defined herein and where the composition acts on the effects of light radiation on the skin and/or of its appendages, and more particularly the effects of blue light to fight against harmful effects and in a particularly advantageous manner at the same time to increase the beneficial effects by resynchronizing the circadian cycle.

19 Claims, No Drawings

Specification includes a Sequence Listing.

SEQUENCE LISTING

```
<160> NUMBER OF SEQ ID NOS: 25

<210> SEQ ID NO 1
<211> LENGTH: 4
<212> TYPE: PRT
<213> ORGANISM: artificial sequence
<220> FEATURE:
<223> OTHER INFORMATION: synthetic peptide

<400> SEQUENCE: 1

Gly Gln Pro Arg
1
```

<210> SEQ ID NO 2
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
terminal end

<400> SEQUENCE: 2

Gly Gln Pro Arg
1

<210> SEQ ID NO 3
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
terminal end

<400> SEQUENCE: 3

Lys Thr Thr Lys Ser
1 5

<210> SEQ ID NO 4
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N
terminal end

<400> SEQUENCE: 4

Val Gly Val Ala Pro Gly
1 5

<210> SEQ ID NO 5
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Palmitoyl chain on the N
terminal end

<400> SEQUENCE: 5

Lys Thr Phe Lys
1

<210> SEQ ID NO 6
<211> LENGTH: 4
<212> TYPE: PRT
<213> ORGANISM: artificial sequence
<220> FEATURE:

<223> OTHER INFORMATION: synthetic peptide

<400> SEQUENCE: 6

Arg Ser Arg Lys
1

<210> SEQ ID NO 7
<211> LENGTH: 4
<212> TYPE: PRT
<213> ORGANISM: artificial sequence
<220> FEATURE:
<223> OTHER INFORMATION: peptidic compound

<400> SEQUENCE: 7

Lys Thr Phe Lys
1

<210> SEQ ID NO 8
<211> LENGTH: 4
<212> TYPE: PRT
<213> ORGANISM: Artificial sequence
<220> FEATURE:
<223> OTHER INFORMATION: Synthetic peptide

<400> SEQUENCE: 8

Lys Thr Ala Lys
1

<210> SEQ ID NO 9
<211> LENGTH: 4
<212> TYPE: PRT
<213> ORGANISM: Artificial sequence
<220> FEATURE:
<223> OTHER INFORMATION: Synthetic peptide

<400> SEQUENCE: 9

Lys Ala Tyr Lys
1

<210> SEQ ID NO 10
<211> LENGTH: 4
<212> TYPE: PRT
<213> ORGANISM: Artificial sequence
<220> FEATURE:
<223> OTHER INFORMATION: Synthetic peptide

<400> SEQUENCE: 10

Lys Phe Tyr Lys
1

<210> SEQ ID NO 11
<211> LENGTH: 5
<212> TYPE: PRT
<213> ORGANISM: artificial sequence
<220> FEATURE:
<223> OTHER INFORMATION: synthetic peptide

<400> SEQUENCE: 11

Lys Thr Thr Lys Ser
1               5

<210> SEQ ID NO 12
<211> LENGTH: 6
<212> TYPE: PRT
<213> ORGANISM: artificial sequence
<220> FEATURE:
<223> OTHER INFORMATION: synthetic peptide

<400> SEQUENCE: 12

Gly Lys Thr Thr Lys Ser
1 5

<210> SEQ ID NO 13
<211> LENGTH: 6
<212> TYPE: PRT
<213> ORGANISM: artificial sequence
<220> FEATURE:
<223> OTHER INFORMATION: synthetic peptide

<400> SEQUENCE: 13

Val Gly Val Ala Pro Gly
1 5

<210> SEQ ID NO 14
<211> LENGTH: 4
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Elaidoyl chain on the N terminal end

<400> SEQUENCE: 14

Lys Thr Phe Lys
1

<210> SEQ ID NO 15
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Elaidoyl chain on the N terminal end

<400> SEQUENCE: 15

Lys Thr Ala Lys
1

<210> SEQ ID NO 16
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Elaidoyl chain on the N terminal end

<400> SEQUENCE: 16

Lys Ala Tyr Lys
1

<210> SEQ ID NO 17
<211> LENGTH: 4
<212> TYPE: PRT
<213> ORGANISM: Artificial sequence
<220> FEATURE:

-continued

<223> OTHER INFORMATION: Synthetic peptide
<220> FEATURE:
<221> NAME/KEY: MOD_RES
<222> LOCATION: (1)..(1)
<223> OTHER INFORMATION: amidation by a Elaidoyl chain on the N terminal end

<400> SEQUENCE: 17

Lys Phe Tyr Lys
1

<210> SEQ ID NO 18
<211> LENGTH: 5
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N terminal end
<220> FEATURE:
<221> NAME/KEY: MISC_FEATURE
<222> LOCATION: (5)..(5)
<223> OTHER INFORMATION: Xaa being either a Proline P or a Leucine L.

<400> SEQUENCE: 18

Tyr Gly Gly Phe Xaa
1 5

<210> SEQ ID NO 19
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: amidation by a Palmitoyl chain on the N terminal end

<400> SEQUENCE: 19

Gly Lys Thr Thr Lys Ser
1 5

<210> SEQ ID NO 20
<211> LENGTH: 6
<212> TYPE: PRT
<213> ORGANISM: Artificial sequence
<220> FEATURE:
<223> OTHER INFORMATION: Synthetic peptide
<220> FEATURE:
<221> NAME/KEY: MOD_RES
<222> LOCATION: (1)..(1)
<223> OTHER INFORMATION: amidation by a Palmitoyl chain on the N terminal end
<220> FEATURE:
<221> NAME/KEY: MISC_FEATURE
<222> LOCATION: (6)..(6)
<223> OTHER INFORMATION: Xaa being Trp, Phe, Tyr, Tic, 7-hydroxy-Tic or Tpi

<400> SEQUENCE: 20

His Leu Asp Ile Ile Xaa
1 5

<210> SEQ ID NO 21
<211> LENGTH: 6
<212> TYPE: PRT

-continued

<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: Acetylation on the N-terminal end

<400> SEQUENCE: 21

Glu Glu Met Gln Arg Arg
1 5

<210> SEQ ID NO 22
<211> LENGTH: 5
<212> TYPE: PRT
<213> ORGANISM: artificial sequence
<220> FEATURE:
<223> OTHER INFORMATION: synthetic peptide

<400> SEQUENCE: 22

Tyr Ala Gly Phe Leu
1 5

<210> SEQ ID NO 23
<211> LENGTH: 4
<212> TYPE: PRT
<213> ORGANISM: artificial sequence
<220> FEATURE:
<223> OTHER INFORMATION: synthetic peptide

<400> SEQUENCE: 23

Ala His Ser His
1

<210> SEQ ID NO 24
<211> LENGTH: 6
<212> TYPE: PRT
<213> ORGANISM: artificial sequence
<220> FEATURE:
<223> OTHER INFORMATION: synthetic peptide

<400> SEQUENCE: 24

Ser Ile Lys Val Ala Val
1 5

<210> SEQ ID NO 25
<211> LENGTH: 6
<212> TYPE: PRT
<213> ORGANISM: artificial sequence
<220> FEATURE:
<223> OTHER INFORMATION: synthetic peptide

<400> SEQUENCE: 25

Gly Pro Gln Gly Pro Gln
1 5

COSMETIC OR DERMATOLOGICAL COMPOSITION ACTING IN PARTICULAR ON THE EFFECTS OF BLUE LIGHT ON SKIN AND ITS APPENDAGES, AND ASSOCIATED USES

CROSS-REFERENCE TO RELATED APPLICATIONS

This application is a U.S. National Phase application of PCT International Application No. PCT/EP2020/086037, filed Dec. 14, 2020, which claims priority to French Patent Application No. 1915141, filed Dec. 20, 2019, each of which is incorporated by reference herein in its entirety for all purposes.

TECHNICAL FIELD

The present invention relates to a cosmetic or dermatological composition acting on the effects of blue light on the skin and its appendages, and the associated uses. In particular, it aims the cosmetic, dermatological, hygiene and personal care products industries (for humans and animals).

BACKGROUND ART

Exposure to sunlight has long been identified as a factor that increases the risk of skin wrinkles, age spots and sagging. Damages caused to the skin and its appendages by the sun is photochemical in nature, inducing biochemical disturbances on living molecules, such as DNA, lipids, proteins and sugars, and causing damages to cellular organelles. Until recently, almost only the effects of UVA (320 to 400 nm) and UVB (280 to 320 nm) were studied because these radiations are the most energetic and therefore more photoreactive. These two types of radiation (UV A and B) are known to act differently on the living. No particular attention was paid on the effects of visible light, considered little dangerous because less energetic.

Visible light is the region of the sunlight spectrum ranging from 400 to 700 nm, blue light ranging from 400 to 500 nm, encompassing violet, indigo and blue. Blue light is close to UVA in terms of wavelength, but its action is different at least in part. This is the most energetic part of the visible spectrum, called "High Energy Visible Light" and because of its wavelength, blue light radiations will penetrate deeper into the skin than UVA radiations.

Visible radiations, at natural doses, have a beneficial effect on the organism. They are necessary for the organism to produce relaxing endorphins and for daily resynchronization of the circadian rhythm (including all cyclic biological processes lasting about 24 hours). This beneficial effect is manifested in particular by an action at the level of opsins (OPN) which are membrane proteins that capture light energy and which, thus excited, will ensure the control of melatonin production and in particular the expression of the Period2circadian protein encoded by the PER2 gene. In women, the OPN 5 is present in the basal part of the epidermis. OPN 5 is stimulated by blue light and plays a beneficial role in the synchronization of cutaneous circadian genes. The PER2 gene thus follows a production rhythm in the form of a wave, increasing in the morning and decreasing at night. This process is markedly reduced among aged people. It is now known that OPN5, and the proteins of the circadian rhythm which OPN5 controls the expression, play a determining role in the effective functioning of skin. Among the known effects in this sense, it can be cited: the stabilization of the intracellular production of oxygenated radical species (ROS) and pro-inflammatory cytokines, a better skin hydration associated with a more effective barrier function and a decrease in the level and the activity of MMP1 (the main collagen degrading enzyme). This shows the interest for the skin to present a high level of OPN5 and of the Period2 circadian protein.

However, these visible radiations can also have negative effects at too high dose.

In an increasingly connected world, the amount of artificial blue light, particularly blue light emitted by screens, to which we are subjected constitutes a new type of pollution, i.e. digital pollution. The light from the screens tires and makes your eyes squint, frowning, which produces fine lines. It gives a dull complexion and accelerates skin aging. Excessive exposure accelerates the signs of aging, increases of shriveled aspect of skin by modifying fine wrinkles, reduces its hydration, causes micro-inflammations, altering the skin barrier and the underlying dermis.

The deleterious effects of blue light at the cellular level are beginning to be better understood. Blue light stimulates the production of $H_2O_2$ and oxygenated free radical species (ROS) by peroxisomes and mitochondria. In addition, a decrease in energy production in the mitochondria has been observed. A decrease in the proliferative capacity of fibroblasts and keratinocytes by blue light has also been described. Studies on epidermal equivalents have shown that exposure to blue light induced increased production of ROS, MMP-1 (protease responsible for the degradation of collagen I) and proinflammatory interleukins.

One of the particularly negative effects of blue light is also the effect that operates on melatonin, a molecule produced by the skin at night and known for its circadian rhythm regulating effect (for example, facilitating falling asleep). Too much blue light disturbs the production of melatonin. A few hours after exposure to blue light there is a sharp drop in the circulating melatonin in volunteers. But melatonin has positive effects. It has a direct antioxidant effect which reduces the toxicity of chemical molecules. It stimulates the mitochondrial electronic transport chain and the associated ATP production with consequently a decrease in the $H_2O_2$ production and its transformation into OH° as well as less $H_2O_2$ leakage into the rest of the cell. Besides, melatonin can stimulate the activity of antioxidant enzymes such as superoxide dismutase (SOD), catalase and glutathione peroxidase involved in the detoxification of $H_2O_2$. In addition, melatonin and its by-products show pro-differentiating activities in the keratinocyte. Yet it is known that this contributes favorably to the establishment of the barrier, to the maintenance of epidermal balance and to the protection regarding sun of the skin.

Therefore, melatonin is potentially an anti-aging agent, and especially if it is produced in situ and not supplied exogenously. Guaranteeing a good skin level of melatonin allows to act locally and effectively on the harmful productions of ultraviolet or blue light radiations.

Ingredients active on the harmful effects of blue light for cosmetic products have already been proposed, for example:

- PHYTOBIOACTIF SOLIBERINE® of Greentech (*Buddleja officinalis*) which protects skin against the deleterious effects of light rays, especially blue light.
- BLUESHIELD® of SOLABIA, based on pepper, an antioxidant active which protects the photoreceptors from light stress.

SUMMARY OF THE INVENTION

The object of the present invention is to provide a cosmetic or dermatological composition capable of acting on the effects of light radiations, in particular on the effects of blue light.

To this end, the present invention provides a cosmetic or dermatological composition comprising, or consisting of:

Chrysin;

Rosmarinic acid;

At least one peptide or derivative thereof, having a sequence of 4 to 10 amino acids comprising the active sequence GQPR (SEQ ID NO 1); and A physiologically acceptable medium, the at least one derivative corresponding to said modified peptide:

At the N-terminal end by an acyle (—CO—$R^1$), a sulfonyle (—$SO_2$—$R^1$) or a biotinoyle group; and/or At the C-terminal end by an $OR^1$, $NH_2$, $NHR^1$ or $NR^1R^2$;

$R^1$ and $R^2$ being, independently of one another, chosen from an alkyl, aryl, aralkyl, alkylaryl, alkoxy, saccharide and aryloxy group, which may be linear, branched, cyclic, polycyclic, unsaturated, hydroxyl, carbonyl, phosphorylated and/or sulfur-containing, said group having from 1 to 24 carbon atoms and possibly having in its backbone one or more 0, S and/or N heteroatoms.

Advantageously, the inventors have shown that a composition according to the invention acts on the effects of light radiations on the skin and/or of its appendages, and more particularly acts on the effects of blue light. In particular preventing and fighting against the harmful effects of blue light is obtained thanks to the invention and, in a particularly advantageous manner, at the same time an increase of the beneficial effects of blue light, in particular by resynchronizing the circadian cycle. In addition, and surprisingly, a synergy between the three components of the composition according to the invention has been demonstrated in an inhibition test of an inflammation marker described below.

More particularly and as shown by the tests given below, the composition according to the invention for example allows the skin to take advantage of the benefits of blue light by stimulating the synthesis of Opsin 5 which, as explained above, represents one of the photoreceptors of blue light synchronizing the circadian cycle and strengthening epidermal homeostasis.

In addition, by its ability to produce melatonin in skin cells, the composition according to the invention the skin can effectively combat against the deleterious actions of blue light (oxidation, inflammation, dermal degradation, dysfunction at the level of mitochondria, etc.).

This action at the cellular level can limit the effects of high exposures on skin, in particular exposure to blue light: dull complexion, skin fatigue, accelerated aging.

According to preferred features:

The chrysin is present at a concentration ranging from 0.2 to 20,000 ppm in weight, preferably from 2 to 2,000 ppm in weight, with regard to the total weight of the composition;

The rosmarinic aci is present at a concentration ranging from 0.1 to 10,000 ppm in weight, preferably from 1 to 1,000 ppm in weight, with regard to the total weight of the composition; and/or The peptide is present at a concentration ranging from 0.5 to 50,000 ppm in weight, preferably from 5 to 5,000 ppm in weight, with regard to the total weight of the composition.

The present invention concerns the use of chrysin (5,7-dihydroxyflavone). It also covers its analogues and derivatives. A chrysin analogue having a flavonoid or flavone structure is encompassed, preferably a substituted flavone-5,7 structure (in particular, quercetin, apigenin, luteolin or diosmetin). As derivatives, mention may be made of techtochrysin and 5-methylether chrysin. Chrysin or one of its analogues or derivatives can be supplied in the form of a plant extract, which can be, for example, an extract of *Oroxylum indicum.*

Rosmarinic acid can also be provided in the form of a plant extract, in particular chosen from rosemary (*Rosmarinus officinalis*), lemongrass, sages, basil, mints, perilla, brunelle, orthosiphon, lavenders, comfrey, savory, horehound, hyssop, monarda, many plants of the Labiee (especially), Boraginaceae and Apiaceae families, preferably in the form of a *Rosmarinus officinalis* extract. Chrysin and rosmarinic acid are known especially in cosmetics for their antioxidant and anti-inflammatory properties.

According to other preferred features:

The peptide or derivative thereof comprises 4 to 8 amino acids, preferably 4 to 6 amino acids and more preferably 4 amino acids corresponding to the sequence GQPR (SEQ ID NO 1), the amino acids outside the GQPR sequence (SEQ ID NO 1) when they are present, being preferably chosen from among the 20 natural amino acids; and/or $R^1$ and/or $R^2$ correspond to an alkyl chain of 3 to 24 carbon atoms; and/or The derived peptide comprises a single modification at the N-terminal position corresponding to an acyl group CO—$R^1$; and/or The acyl group —CO—$R^1$ is chosen from an octanoyl (C8), decanoyl (C10), lauroyl (C12), myristoyl (C14), palmitoyl (C16), stearoyl (C18), biotinoyl, elaidoyl, oleoyl and lipoyl.

The peptide according to the invention may be optically pure or consist of the L or D isomers or a mixture thereof. L isomers which are those present in the natural state may be preferred. The peptide may optionally be in the form of a salt, in particular a hydrochloride or acetate.

The peptide can be a natural peptide obtained by extraction and purification or be obtained by chemical synthesis or by biosynthesis via a microorganism, in particular a genetically modified microorganism, for example a microalga. The present invention also covers complexes of said peptide or derivative with other species such as with a metal ion (e.g. copper, zinc, manganese, magnesium, and others).

The peptide according to the invention can also be used in a vectorized form, by being bound, incorporated or adsorbed on/to macro-, micro- or nanoparticles such as capsules, spheres, liposomes, oleosomes, chylomicrons, sponges, in the form of micro- or nano-emulsions, or adsorbed for example on powdery organic polymers, talcs, bentonites, spores or exins and other inorganic or organic supports.

Preferably, the composition comprises the commercial derivative peptide Pal-GQPR (SEQ ID NO 2); INCI name: Palmitoyl Tetrapeptide-7 and more preferably the composition according to the invention comprises or consists of chrysin, an extract of *Rosmarinus officinalis* and Pal-GQPR (SEQ ID NO 2).

Results of in vitro tests are given below in the description. They show the efficiency of the association of the three active ingredients according to the invention by:

A stimulation of the OPS5 production on human keratinocytes (HK) in basal condition or following blue light irradiation;

A stimulation of the Period2 protein production on HK in basal condition;

A stimulation of the melatonin production on HK in basal condition or following blue light irradiation;

The maintaining of the mitochondrial membrane potential on HK following blue light irradiation;

The maintaining or stimulating of the ATP synthesis capacity on HK in basal condition or following blue light irradiation;

An antioxidant action on an experimental model of lipidic membranes exposed to blue light;

A decrease in MMP-1 production on HK following blue light irradiation;

A decrease in two markers of inflammation, PGE-2 and IL-6 on KH following blue light irradiation; and The maintaining of the capacity to contract a collagen gel on human fibroblasts (HF) following blue light irradiation.

Furthermore, an in vivo test carried out on a panel of volunteers, whose facial skin quality is affected by daily contact with blue light from screens, showed the efficacy of a cream containing a composition according to the invention for improving hydration, smoothness, radiance and tone of their skin.

Thus, the present invention also proposes the use of a composition according to the invention for a non-therapeutic cosmetic treatment of the skin and/or its appendages, in particular a treatment for preventing or treating the effects of photoaging.

More particularly, the use of the composition according to the invention is proposed for both preventing and/or treating the harmful effects of blue light and/or for increasing the beneficial effects thereof. The treatment improves hydration, smoothness, radiance and/or skin tone. The treatment is preferably topical.

"Physiologically acceptable medium" means according to the present invention, without limitation, an aqueous or hydro-alcoholic solution, a water-in-oil emulsion, an oil-in-water emulsion, a microemulsion, an aqueous gel, an anhydrous gel, a serum, a dispersion of vesicles, or a powder.

"Physiologically acceptable" means that the compositions are suitable for topical or transdermal use, in contact with mucous membranes, appendages (nails, hairs), scalp and skin of mammals, particularly human, compositions which may be ingested, or injected into the skin, without risk of toxicity, incompatibility, instability, allergic response, and others. This "physiologically acceptable medium" forms what is commonly called the excipient of the composition.

Any type of physiologically acceptable medium known to those skilled in the art can be envisaged to dissolve the active agents and to formulate the ingredient according to the invention. For example: an aqueous, alcoholic or hydroalcoholic, glycolic or hydro-glycolic solution, a water-in-oil emulsion, an oil-in-water emulsion, a microemulsion, an aqueous gel, an anhydrous gel, a serum, a dispersion of vesicles or a powder.

Furthermore, the composition of the invention can be used under a vectorised form, being bound, incorporated or adsorbed on/to macro-, micro-, or nano-particles such as capsules, spheres, liposomes, oleosomes, chylomicrons, sponges, in the form of micro- or nano-emulsions, or adsorbed for example on organic polymer powders, talcs, bentonites, spores or exines, and other inorganic or organic supports.

A composition according to the invention can be provided in any galenic form (examples are given below in the description) and also be conveyed via a textile support made of natural or synthetic fibers, wool, or any material suitable for use in contact with skin, or which can be used in clothing, such as day or night underwear, handkerchiefs, or fabrics, in order to exert its cosmetic or dermatological effect through this skin contact/textile and allow continuous topical delivery.

In a particular and advantageous manner, according to the invention, the composition may comprise one or more additional active agents suitable for acting in reinforcing activity and/or for acting in a complementary manner on one or more other activities.

Various additional actives for this purpose are mentioned below in the detailed description.

According to the invention, a method is further provided for improving the aesthetic appearance of the skin and of its appendages comprising the topical application to the skin of an effective amount of a cosmetic or dermatological composition according to the invention such as described above.

According to the invention, by "topical treatment" or "topical use" is meant an application which is intended to act at the place where it is applied: skin, mucous membrane, appendages.

The composition according to the invention may be applied locally to targeted areas.

The "effective" amount depends on various factors, such as the age, the condition of the patient, the seriousness of the disorder or pathology, the administration mode, etc. An effective amount means a non-toxic amount enough to achieve the desired effect All percentages and ratios used herein are by weight of the total composition and all measurements are made at 25° C. unless it is otherwise specified.

For example, for a cosmetic treatment of the face, the European Cosmetics Directive has set a standard amount for applying a cream of 2.72 $mg/cm^2$/day/person and for a body lotion of 0.5 $mg/cm^2$/day/person.

According to other specific features, the cosmetic treatment method according to the invention can be combined with one or more other treatment methods targeting the skin such as lumino-therapy, heat, vibrations, electroporation, micro-needle patch or aromatherapy.

According to the invention, devices with several compartments or kits may be proposed to apply the method described above which may include for example and non-restrictively, a first compartment containing an active ingredient according to the invention, and in a second compartment another active ingredient and/or excipient, the compositions contained in the said first and second compartments in this case being considered to be a combination composition for simultaneous, separate or stepwise use in time, particularly in one of the treatment methods recited above.

A composition according to the invention is also suitable for a therapeutic treatment of the skin at suitable doses.

DETAILED DESCRIPTION

The present invention will be better understood in the light of the following description of an embodiment and in vitro and in vivo tests.

A/ Example of Preparation of a Preferred Composition According to the Invention, Forming a Concentrated Ingredient being the Combination of the Three Active Ingredients According to the Invention, Intended for the Manufacture of a Galenical Formulation (See Paragraph D/)

The ingredient comprises:

The chrysin:

Origin: synthetic, pure at at least 94%

Chrysin final concentration in the composition: 200 ppm

The rosmarinic acid:

Origin: a leaf extract of *Rosmarinus officinalis* (rosmary) comprising at least 6% of rosmarinic acid.

Rosmarinic acid final concentration in the composition: 60 ppm

The Palmitoyl-GQPR-OH (SEQ ID NO 2), pure at at least 99%

Origin: synthetic

Palmitoyl-GQPR-OH (SEQ ID NO 2) final concentration in the composition: 750 ppm

Excipient: glycolic type.

B/ Synergy Test

Protocol

HK are cultivated in their culture medium. After rinsing with PBS, the cells are returned to this same buffer and exposed to blue light at a non-cytotoxic dose of 30.2 $J/cm^2$. The exhibition system consists of a set of 30 blue LEDs spread over a 30 $cm^2$ flat surface. The photon flux reaches the cells perpendicularly. The temperature is controlled, and all the cells are in the same enclosure (37° C./5% $CO_2$). The emission spectrum is centered on 420 nm. The cells are then brought into contact with each of the invention compounds taken separately or with the composition according to the invention for 24 hours. The culture media are then harvested, and the IL-6 concentrations assayed by ELISA method. An assay on the cell layers is used to reduce to the number of cells.

Results

Variation in IL-6 production on HK following blue light irradiation; effect of the composition according to the invention compared to the sum of the effects of the compounds of the composition taken separately.

TABLE 1

| Compound | Concentration | % of variation |
|---|---|---|
| Compound taken separately: | | |
| Extract of rosmary leaf at 6% of rosmarinic acid in ppm | 17 ppm | −13% (nsd) |
| Pal-GQPR | 15 ppm | −7% (nsd) |
| Chrysine | 1.6 ppm | −10% (nsd) |
| Compounds associated according to the invention | | |
| Rosmarinic acid + Chrysine + Pal-GQPR | 17 ppm + 15 ppm + 1.6 ppm | −41% ($p < 0.01$) |

nsd = non significative difference.

These results show a synergistic effect when the three compounds are combined here to combat the effects of blue light. The improvement in the inhibition of IL-6 production is 46.2% ($p<0.01$) for the composition according to the invention compared to the sum of the three compounds tested separately.

C/ In-Vitro Efficacy Tests of the Composition According to the Invention

They were carried out on an equivalent of the preferred composition according to the invention: 750 ppm of Palmitoyl-GQPR-OH (SEQ ID NO 2), 200 ppm of chrysin and 1000 ppm of a rosemary extract (equivalent to 60 ppm of rosmarinic acid in the composition). This equivalent was used at 0.5, 1 or 2% in the tests on human fibroblasts (HF). These concentrations are within the range of concentrations recommended for an active ingredient in a cosmetic product to be applied to the skin.

TABLE 2

| | Composition at 0.5% | Composition at 1% | Composition at 2% |
|---|---|---|---|
| Pal-GQPR in ppm | 3.75 | 7.5 | 15 |
| Chrysine in ppm | 1 | 2 | 4 |
| Extract of rosmary leaf at 6% of rosmarinic acid in ppm | 5 | 10 | 20 |

For tests on human keratinocytes (HK), in vitro tests were carried out on an equivalent of the composition according to the invention: 750 ppm of Palmitoyl-GQPR, 80 ppm of chrysin and 1000 ppm rosemary extract (equivalent to 60 ppm of rosmarinic acid in the composition). This equivalent was used at 0.5, 1 or 2%. These concentrations are in the range of concentrations recommended for an active ingredient in a cosmetic composition for application to the skin.

TABLE 3

| | Composition at 0.5% | Composition at 1% | Composition at 2% |
|---|---|---|---|
| Pal-GQPR in ppm | 3.75 | 7.5 | 15 |
| Chrysine in ppm | 0.4 | 0.8 | 1.6 |
| Extract of rosmary leaf at 6% of rosmarinic acid in ppm | 5 | 10 | 20 |

Chrysin and Pal-GQPR were presolubilized in DMSO (at 1000 times the final concentration in the test) before being introduced into the aqueous test media. The rosemary leaf extract is directly soluble in aqueous media.

1/ Decrease in Intracellular Radical Species

Protocol

Normal human fibroblasts (HNF) are grown to confluence in their culture medium. The cells are then brought into contact with the composition according to the invention for 24 hours and then receive a fluorescent probe intended to mark the ROS intracellular production.

After incorporation for 30 min and rinsing, the cells receive again the composition according to the invention and either nothing or an agent intended to create ROS (oxidative stress). The quantity of intracellular ROS is estimated by a fluorescence reading (eg: 490 nm/em: 520 nm). The number of cells is estimated using the Hoescht 33258 method (DNA staining) to weight the data obtained.

Results

Variation in the production of ROS on NHFs with or without oxidative stress (n=3)

TABLE 4

| Studied case | Variation (%) | Variation (%) |
|---|---|---|
| Control | Reference 1 | |
| Composition according to the | −66%; | |

TABLE 4-continued

| Studied case | Variation (%) | Variation (%) |
|---|---|---|
| invention 0.5% | p < 0.01 | |
| Composition according to the invention 1% | −69%; p < 0.01 | |
| Control, oxidative stress | +284%; p < 0.01 | Reference 2 |
| Composition according to the invention 0.5%, oxidative stress | | −83%; p < 0.01 |
| Composition according to the invention 1%, oxidative stress | | −82%; p < 0.01 |

These results show that the composition according to the invention reduces the intracellular content of ROS, either under basal conditions or under oxidative stress conditions. In both cases, these decreases are important and significant, which shows the interest of the composition according to the invention for combating the appearance of intracellular ROS known for their involvement in skin aging.

2/ Production of Opsine-5 (OPN5)

2.1/ Assay by qRT-PCR (Quantitative Real Time Reverse Transcription Polymerase Chain Reaction)

Protocol

Sub-confluent HK are synchronized (all brought to the same phase of the cell cycle) by exposure for 2 hours in DMEM culture medium containing 50% serum. After rinsing with PBS, the cells are returned to this same buffer and exposed to blue light at a non-cytotoxic dose of 30.2 J/cm$^2$. The exposure system is identical to that described above in B). At the end of the exposure, the irradiated or non-irradiated cells are brought into contact with the composition according to the invention for 3 hours. The total RNAs are then extracted and the expression of the gene encoding OPN5 is evaluated by the qRT-PCR molecular biology method.

Results

Variation in the expression of OPN5 in HK after 3 hours of contact with the composition according to the invention (n=3)

TABLE 5

| Studied case | Variation (%) |
|---|---|
| Control, not irradiated | Reference |
| Composition according to the invention 1%, not irradiated | +158%; p < 0.01 |
| Composition according to the invention 2%, not irradiated | +246%; p < 0.01 |
| Control, blue light | +182%; p < 0.01 |
| Composition according to the invention 1%, blue light | +226%; p < 0.01 |
| Composition according to the invention 2%, blue light | +479%; p < 0.01 |

These results clearly show that blue light can, in vitro, favorably modulate the expression of the gene encoding the OPN5 protein in HK (+182% for the control). They also show that the composition according to the invention strongly stimulates, with or without blue light, the expression of the OPN5 gene, compared to the control.

2.2/ Assay by Immunocytochemistry

Protocol

The same culture and irradiation protocol (or not for non-irradiated cases) as above (2.1/) is carried out on HK. The cells, irradiated or not, are brought into contact with the composition according to the invention (or nothing for the control) for 12 hours. Next, the cell layers are labeled with an anti-OPN5 protein antibody. Photos are taken and the resulting images analyzed and compared. Counter-labeling of the nuclei using the Hoescht 33258 method (DNA staining) is used for countering the cells and to weight the results.

Results

Variation in the expression of OPN5 in HK after 12 hours of contact with the composition according to the invention (4 cultures/case and 16 photos/culture).

TABLE 6

| Studied case | Variation (%) |
|---|---|
| Control, not irradiated | Reference |
| Composition according to the invention 1%, not irradiated | +98%; p < 0.01 |
| Composition according to the invention 2%, not irradiated | +106%; p <0.01 |
| Control, blue light | +62%; p < 0.01 |
| Composition according to the invention 1%, blue light | +224%; p < 0.01 |
| Composition according to the invention 2%, blue light | +212%; p < 0.01 |

These results confirm the data obtained in molecular biology:

- Exposure to blue light increases the production of OPN5 in the control; and
- Contact of the cells, with or without irradiation, with the composition according to the invention increases this production compared to the control.

3/ Production of Period2, Protein of the Circadian Cycle

Protocol

The same as that described above in 2.1/. At the end of the exposure (of only the control cases), the non-irradiated cells are brought into contact with the composition according to the invention (or nothing for the controls). The total RNAs are extracted at 3 h, then the expression of the gene encoding PER2 is evaluated by qRT-PCR.

Results

Variation in the expression of PER2 in HK after 3 hours of contact with the composition according to the invention (n=3)

TABLE 7

| Studied case | Variation (%) |
|---|---|
| Control, not irradiated | Reference |
| Composition according to the invention 1%, not irradiated | +32%; p < 0.01 |
| Composition according to the invention 2%, not irradiated | +29%; p < 0.01 |
| Control, blue light | +84%; p < 0.01 |

These results show that blue light stimulates the production of PER2 in cultured cells. This confirms that these cells have the adapted chromophores. Advantageously, it is seen that PER2 is also stimulated by contacting the cells with the composition according to the invention, but without the need for exposure to blue light.

4/ Production of Melatonine

Protocol

The same as that described above in 2.1/. At the end of the exposure, the irradiated or non-irradiated cells are brought into contact with the composition according to the invention (or not for the controls). All cultures are stopped 12 hours later. The culture media are removed and the amount of melatonin is assayed by ELISA. The results are normalized using the amounts of total RNA found in the cell layers of each sample.

Results

Variation in the production of melatonin in HK after 12 hours of contact with the composition according to the invention (n=3)

TABLE 8

| Studied case | Variation (%) | Variation (%) |
|---|---|---|
| Non-irradiated control | Reference 1 | |
| Composition according to the invention 1% | +31%; dns | |
| Composition according to the invention 2% | +71%; p < 0.02 | |
| Control, blue light | −38%; p < 0.02 | Reference 2 |
| Composition according to the invention 1%, blue light | | +106%; p < 0.01 |
| Composition selon Tinvention 2%, blue light | | +218%; p < 0,01 |

These results show that blue light decreases melatonin production for 38% in the selected irradiation system (p<0.02). This appears to be linked to the direct or indirect intracellular production of ROS by blue light which "consumes" this natural antioxidant resource. In contrast, the composition according to the invention, with or without irradiation, stimulates production of this natural anti-aging molecule. The stimulation is in both cases dose-dependent and significant. The composition according to the invention presents therefore a dual effect: it fights effectively against ROS and also stimulates the production of an intracellular antioxidant.

5/ Mitochondrial Membrane Potential

Protocol

HK are grown to confluence in their culture medium. Once placed in an appropriate buffer, the cells are exposed to blue light as mentioned previously (in B/). The cells are then placed in contact with the composition according to the invention for 25 hours. The mitochondrial membrane potential is then evaluated on living cells by measuring the monomeric cytoplasmic (green) and aggregated (red-yellow) mitochondrial forms of the JC-10 dye at two different wavelengths. A low value of the monomer/aggregate ratio indicates a good state of mitochondria. Staining the nuclei using the Hoescht 33258 method (DNA staining) is used to count the number of cells in order to weight the results.

Results

Variation of mitochondrial membrane potential on HK; effect of the composition according to the invention (25 hours of contact)

TABLE 9

| Sudied case | Variation (%) |
|---|---|
| Control, not irradiated | Reference |
| Control, blue light | +33%; p < 0.01 |
| Composition according to the invention 0.5%, blue light | +2.1%; nsd |

The mitochondrial membrane potential is a gradient of electronic charges resulting from the functioning of the mitochondria. Its disturbance indicates stress and can cause disorders and diseases. The results show that blue light significantly changes the mitochondrial membrane potential in HK. Monomeric forms increase sharply, with respect to the polymers, which increases the ratio of 33% (p<0.01), reflecting a disturbance in the mitochondria. The use of the composition according to the invention, after this irradiation, can maintain the base mitochondrial membrane potential.

6/ Synthesis of Mitochondrial ATP

Protocol

The same protocol as in 5/is followed. After 25 hours of contact with the composition according to the invention (or not for the control cases), the intracellular ATP is extracted and assayed by bioluminescence, the signal obtained being proportional to the amount of ATP in the cells. Staining the nuclei using the Hoescht method (DNA staining) is used to count the number of cells to weight the results.

Results

Variation of ATP pool on HK; effect of the composition according to the invention (25 hours of contact).

TABLE 10

| Studied case | Variation (%) | Variation (%) |
|---|---|---|
| Non irradiated control | Reference 1 | |
| Composition according to the invention 0.5%, not irradiated | +30%; p < 0.01 | |
| Composition according to the invention 1%, not irradiated | +53%; p < 0.01 | |
| Control, blue light | −30%; p < 0.01 | Reference 2 |
| Composition according to the invention 0.5%, blue light | | +33%; p < 0.03 |
| Composition according to the invention 1%, blue light | | +87%; p < 0.01 |

ATP is the energetic building block of living. Metabolisms can function and proteins are manufactured thanks to ATP. Aged or stress-damaged mitochondria produce less energy. The results show that ATP production was depressed following exposure of cells to blue light. This is consistent with what is known and with the observation on the modification of mitochondrial potential. The composition according to the invention, with or without irradiation, stimulates the production of energy in the mitochondria compared to the control case. Without irradiation, the stimulation reached +53% (p<0.01) of the control. With irradiation, it reaches up to +87% (p<0.01) compared to the irradiated control.

7/ Peroxydation of the Lipidic Membranes

Principle

Lipid membranes surround cells and mitochondria. In the latter, they actively maintain the mitochondrial membrane potential. The peroxidation of the membranes weakens them and generates oxygen free radicals by autocatalysis, which amplifies the damages.

Protocol

A model of lipidic membranes of the liposomal type is exposed to blue light (according to the condition described above for the cells in B/). The composition according to the invention is added after irradiation or not (control case). Lipid peroxidation is measured by absorption at 233 nm (absorption wavelength of conjugated dienes).

Results

Measurement of lipid lipoperoxidation on liposomes (model of lipid membranes); effect of the composition according to the invention.

TABLE 11

| Studied case | Variation (%) |
|---|---|
| Control, blue light | Reference |
| Composition according to the invention 0.5%, blue light | −60%; $p < 0.01$ |
| Composition according to the invention 1%, blue light | −68%; $p < 0.01$ |
| Composition according to the invention 2%, blue light | −73%; $p < 0.01$ |

The composition according to the invention strongly and dose-dependently reduces lipid peroxidation. It protects lipid membranes against the oxidative damages of blue light.

8/ Expression of the Gene of MMP-1

Protocol

HK are grown to confluence in their culture medium. Once placed in an appropriate buffer, the cells are exposed to blue light as mentioned above (B/), then brought into contact with the composition according to the invention for 6 hours. The total RNAs are extracted, quantified and analyzed by transcriptomic study on mRNA chips. Ten copies of the detection probe for the MMP1 gene are present in the mRNA chips and two biological replicas are quantified, i.e. one n=20 per condition.

Results

Variation in the expression of the MMP-1 gene on HK, effect of the composition according to the invention (6 hours of contact).

TABLE 12

| Studied case | Variation (%) | Variation (%) |
|---|---|---|
| Not irradiated control | Reference 1 | |
| Control, blue light | +205%; $p < 0.01$ | Reference 2 |
| Composition according to the invention 2%, blue light | | −35%; $p < 0.01$ |

These results clearly show that in the studied irradiation system, blue light induces an increase of 205% ($p<0.01$) of the expression of the MMP1 gene encoding the eponymous protein. On the contrary, the composition according to the invention, at 2%, after irradiation of the cells with blue light, slows down the production of this molecule which is strongly involved in the phenomena of degradation of extracellular matrices.

9/ Production of Inflammation Mediators

Protocol

HK are cultivated in their culture medium. Once placed in an appropriate buffer, the cells are exposed to blue light as mentioned previously (B/). The cells are then brought into contact with the composition according to the invention for 24 hours. The culture media are then harvested, then the IL-6 and PGE2 concentrations assayed by the ELISA method. An assay on the cell layers is used to reduce to the number of cells.

Results

Variation of IL-6 protein expression on HK; effect of the composition according to the invention (24 hours of contact).

TABLE 13

| Studied case | Variation (%) | Variation (%) |
|---|---|---|
| Non irradiated control | Reference 1 | |
| Control, blue light | +147%; $p < 0.01$ | Reference 2 |
| Composition according to the invention 2%, blue light | | −57%; $p < 0.01$ |

Variation in the expression of the pro-inflammatory lipid PGE-2 on HK; effect of the composition according to the invention (24 hours of contact).

TABLE 14

| Studied case | Variation (%) | Variation (%) |
|---|---|---|
| Non irradiated control | Reference 1 | |
| Control, blue light | +108%; $p < 0.01$ | Reference 2 |
| Composition according to the invention 0.5%, blue light | | −59%; $p < 0.01$ |
| Composition according to the invention 1%, blue light | | −68%; $p < 0.01$ |
| Composition according to the invention 2%, blue light | | −72%; $p < 0.01$ |

These results (Tables 11 and 12) clearly show that blue light induces an increase in the synthesis of cytokine IL-6 and PGE2 of 147% and 108% respectively (both $p<0.01$). On the contrary, the composition according to the invention, after irradiation of the cells with blue light, inhibits the syntheses of these pro-inflammatory molecules. These inhibitions are significant and dose dependent in the case of PGE2.

10/ Post-Stress Cellular Resilience

Protocol

NHF are cultured until confluence in their culture medium and then irradiated with blue light (as in B/) before being brought into contact with the composition according to the invention for 24 hours. The cells are then detached and included in collagen gels to form a dermis equivalent. The contraction of the gels by the cells is monitored. The areas of the gels are measured and the delta of the areas versus TO calculated for each condition.

Results

Variation of the contraction of collagen gels by HF; effect of the composition according to the invention (24 hours of contact).

TABLE 15

| Studied case | Variation (%) | Variation (%) |
|---|---|---|
| Non irradiated control | Reference 1 | |
| Control, blue light | −36%; $p < 0.01$ | Reference 2 |
| Composition according to the invention 0.5%, blue light | | +32%; $p < 0.01$ |
| Composition according to the invention 1%, blue light | | +121%; $p < 0.01$ |

These results show that blue light decreases the capacity of fibroblasts to contract collagen gels (−36%). They also show that the composition according to the invention, despite irradiation with blue light, maintains the force of contraction of fibroblasts. This indicates the skin's capacity to maintain its resiliency when facing this stress.

D/ Galenic/Preparation of a Composition According to the Invention

A composition according to the invention may comprise additional cosmetic active ingredients, which may come as a support and/or activity complement, either in the ingredient form, or at the time of the production of the final cosmetic composition for the consumer. This composition can be applied to the face, body, neckline, scalp, hair, eyelashes, body hair, nails, lips, in any form or vehicles known to those skilled in the art, in particular in the form of a solution, dispersion, emulsion, paste or powder, individually or as a premix or be conveyed individually or as a premix.

In cosmetics, applications can be offered in particular in the skin care ranges for the face, body, hair and body hair and in makeup-care ranges.

These additional active agents can be of any category according to their function(s), the place of application (body, face, neck, bust, hands, hair, eyelashes, eyebrows, body hair, nails, lips, etc.), the desired final effect and the targeted consumer, for example antioxidant, tightening, moisturizing, nourishing, protective, smoothing, remodeling, volumizing (lipofiling), acting on the radiance of the complexion, anti-dark spots, anti-dark circles, anti-glycation, anti-aging, anti-wrinkle, slimming, soothing, myo-relaxing, anti-redness, anti-stretch marks, sunscreen, etc.

The CTFA («International Cosmetic Ingredient Dictionary & Handbook» (19th Ed. 2019) published by «the Personal Care Products council», ex-«the Cosmetic, Toiletry, and Fragrance Association, Inc.», Washington, D.C.), describes a non-limited wide variety of cosmetic and pharmaceutical ingredients commonly used in the skin care industry, which are suitable for use as additional ingredients in the compositions according to the present invention.

At least one of the following compounds can be cited selected from compounds of the vitamin B3, compounds such as niacinamide or tocopherol, retinoid compounds such as retinol, hexamidine, α-lipoic acid, resveratrol or DHEA, hyaluronic acid, peptides, in particular Pal-KTTKS (SEQ ID NO 3), N-acetyl-Tyr-Arg-O-hexadecyl ester, Pal-VGVAPG (SEQ ID NO 4), Pal-KTFK (SEQ ID NO 5), Pal-GHK, Pal-$KMO_2K$, and/or Pal-K(P)HG (with a proline grafted on the lysine), which are widely used active ingredients in topical cosmetic or dermopharmaceutical compositions.

Further additional skin care actives that are particularly useful can be found in the commercial literature of Sederma and on the website www.sederma.com.

Generally, the following commercial actives can also be mentioned, as examples: betaine, glycerol, Actimoist Bio 2™ (Active organics), AquaCacteen™ (Mibelle AG Cosmetics), Aquaphyline™ (Silab), AquaregulK™ (Solabia), Carciline™ (Greentech), Codiavelane™ (Biotech Marine), Dermaflux™ (Arch Chemicals, Inc), Hydra'Flow™ (Sochibo), Hydromoist L™ (Symrise), RenovHyal™ (Soliance), Seamoss™ (Biotech Marine), Argireline™ (commercial name for the acetyl hexapeptide-3 of Lipotec), spilanthol or an extract of *Acmella oleracea* known under the commercial name Gatuline Expression™, an extract of *Boswellia serrata* known under the commercial name Boswellin™, Deepaline PVB™ (Seppic), Syn-AKE™ (Pentapharm), Ameliox™ Bioxilift™ (Silab), PhytoCellTec™ Argan (Mibelle), Papilactyl D™ (Silab), Preventhelia™ (Lipotec), and from Sederma: Subliskin™, Venuceane™, Moist 24™, Vegesome Moist 24™, Essenskin™, Juvinity™, Revidrat™, Resistem™, Chronodyn™, Kombuchka™, Chromocare™ Calmosensine™, Glycokin factor S™, Biobustyl™, Idealift™, Ceramide 2™, Ceramide A2™ et Ceramide HO3™, Legance™, Intenslim™, Prodizia™, Beautifeye™, NG-shea butter unsaponifiables (natural grade), Zingerslim™, Meiritage™, Senestem™, Sebuless™, Majestem™ Apiscalp™, Rubistem™, Citystem™, Neonyca™, NG Insaponifiables de Beurre de Karité™, Majestem™, Hydronesis™, Poretect™, Crystalide™, Amberstem™, Feminage™, or mixture thereof. Among plant extracts which can be combined with the peptide of the invention, there may more particularly be mentioned extracts of Ivy, in particular English Ivy (*Hedera Helix*), of *Bupleurum chinensis*, of *Bupleurum Falcatum*, of *arnica* (*Arnica Montana* L), of rosemary (*Rosmarinus officinalis* N), of marigold (*Calendula officinalis*), of sage (*Salvia officinalis* L), of ginseng (*Panax ginseng*), of ginko biloba, of St.-John's-Wort (*Hyperycum Perforatum*), of butcher's-broom (*Ruscus aculeatus* L), of European meadowsweet (*Filipendula ulmaria* L), of big-flowered Jarva tea (*Orthosiphon Stamincus* Benth), of algae (*Fucus Vesiculosus*), of birch (*Betula alba*), of green tea, of cola nuts (*Cola Nipida*), of horse-chestnut, of bamboo, of *Centella asiatica*, of heather, of fucus, of willow, of mouse-ear, of escine, of cangzhu, of chrysanthellum indicum, of the plants of the Armeniacea genus, Atractylodis Platicodon, Sinnomenum, Pharbitidis, Flemingia, of *Coleus* such as *C. Forskohlii, C. blumei, C. esquirolii, C. scutellaroides, C. xanthantus* and *C. Barbatus*, such as the extract of root of *Coleus barbatus*, extracts of Ballote, of Guioa, of Davallia, of Terminalia, of Barringtonia, of *Trema*, of antirobia, cecropia, argania, dioscoreae such as *Dioscorea opposita* or Mexican, extracts of *Ammi visnaga*, of Siegesbeckia, in particular *Siegesbeckia orientalis*, vegetable extracts of the family of Ericaceae, in particular bilberry extracts (*Vaccinium angustifollium*) or *Arctostaphylos uva ursi*, aloe vera, plant containing sterols (e.g., phytosterol), Manjistha (extracted from plants of the genus *Rubia*, particularly *Rubia Cordifolia*), and Guggal (extracted from plants of the genus *Commiphora*, particularly *Commiphora Mukul*), kola extract, chamomile, red clover extract, *Piper methysticum* extract (Kava Kava™ from Sederma), *Bacopa monieri* extract (Bacocalmine™ from Sederma) and sea whip extract, extracts of *Glycyrrhiza glabra*, of mulberry, of melaleuca (tea tree), of *Larrea divaricata*, of *Rabdosia rubescens*, of *Euglena gracilis*, of

*Fibraurea recisa* Hirudinea, of Chaparral Sorghum, of sun flower extract, of *Enantia chlorantha*, of Mitracarpe of *Spermacocea* genus, of *Buchu barosma*, of *Lawsonia inermis* L., of Adiantium *Capillus-Veneris* L., of *Chelidonium majus*, of *Luffa cylindrica*, of Japanese Mandarin (*Citrus reticulata* Blanco var. *unshiu*), of *Camelia sinensis*, of *Imperata cylindrica*, of *Glaucium Flavum*, of *Cupressus Sempervirens*, of *Polygonatum multiflorum*, of loveyly hemsleya, of *Sambucus Nigra*, of *Phaseolus lunatus*, of *Centaurium*, of *Macrocystis Pyrifera*, of *Turnera Diffusa*, of *Anemarrhena asphodeloides*, of *Portulaca pilosa*, of *Humulus lupulus*, of *Coffea Arabica*, of *Ilex Paraguariensis*, or of *Globularia Cordifolia*, of *Albizzia julibrissin*, of *Oxydendron arboretum*, of Zingimber Zerumbet Smith, of *Astragalus membranaceus*, of *Atractylodes macrocephalae*, of *Plantago lanceolata*, of *Mirabilis jalapa*, of *Apium graveolens*, of *Marrubium vulgare, Buddleja davidii* Franch, *Engelhardia chrysolepis, Syringa vulgaris* or orchids.

The compositions of the present invention may include one or more additional peptides, including, without limitation, di-, tri-, tetra-, penta- and hexapeptides and their derivatives. According to a particular embodiment, the concentration of the additional peptide, in the composition, ranges from $1\times10^{-7}\%$ and 20%, preferably from $1\times10^{-6}\%$ and 10%, preferably between $1\times10^{-5}\%$ and 5% by weight. The term "peptide" refers here to peptides containing 10 amino acids or less, their derivatives, isomers and complexes with other species such as a metal ion (e.g. copper, zinc, manganese, magnesium, and others). The term "peptides" refers to both natural peptides and synthetic peptides. It also refers to compositions that contain peptides and which are found in nature, and/or are commercially available.

Suitable dipeptides for use herein include but are not limited to Carnosine (βAH), YR, VW, NF, DF, KT, KC, CK, KP, KK, TT, PA, PM or PP.

Suitable tripeptides for use herein include, but are not limited to RKR, HGG, GKH, GHK, GGH, GHG, KGH, KHG, KFK, KAvaK, KβAK, KAbuK, KAcaK, KPK, KMOK, $KMO_2K$ ($MO_2$ being a di-oxygenated sulfoxide methionine), KVK, PPL, PPR, SPR, QPA, LPA, SPA, K(Ac) HG or K(Ac)GH, K(Ac) being a lysine with the amine function of the lateral chain acetylated, as disclosed in WO2017/216177, K(P)HG or K(P)GH, K(P) being a lysine with its lateral chain grafted with a proline, K(Pyr)HG or K(Pyr)GH, K(Pyr) being a lysine with its lateral chain grafted with a pyroglutamic acid, K(Hyp)HG or K(Hyp)GH, K(Hyp) being a lysine with its lateral chain grafted with a hydroxyproline, as disclosed in WO2016/097965.

Suitable tetrapeptides for use as additional peptides herein include but are not limited to RSRK (SEQ ID NO: 6), KTFK (SEQ ID NO: 7), KTAK (SEQ ID NO: 8), KAYK (SEQ ID NO: 9) or KFYK (SEQ ID NO: 10).

A suitable non limitative example of pentapeptide is the KTTKS (SEQ ID NO: 11), and a suitable examples of hexapeptides are the GKTTKS (SEQ ID NO: 12) and VGVAPG (SEQ ID NO: 13).

Other suitable peptides for use according to the present invention can be selected, this list being not limitative, from: lipophilic derivatives of peptides, preferably palmitoyl (Pal) derivatives or myristoyl (Myr), and metal complexes as aforementioned (e.g. copper complex of the tripeptide HGG or GHK). Preferred dipeptides include for example N-Palmitoyl-β-Ala-His, N-Acetyl-Tyr-Arg-hexadecylester (Calmosensine™, Idealift™ from Sederma), Pal-RT or Pal-KT (from Sederma). Preferred tripeptide derivatives include for example Pal-GKH and Pal-GHK (from Sederma), the copper derivative of HGG (Lamin™ from Sigma), Lipospondin (N-Elaidoyl-KFK) and its analogs of conservative substitution, N-Acetyl-RKR-$NH_2$ (Peptide CK+), N-Biot-GHK (from Sederma), Pal-KAvaK, Pal-KβAlaK, Pal-KAbuK, Pal-KAcaK, or Pal-$KMO_2K$ (Matrixyl® synthe'6® from Sederma), Pal-KVK (Syn-Coll™ of DSM), and derivatives thereof.

Mention may also be made here of the anti-aging tripeptides of general Formula X-Pro*-Pro*-Xaa-Y described in WO2015181688 application with Xaa selected from Leu, Arg, Lys, Ala, Ser, and Asp, at the N-terminus, X chosen from H, —CO—$R^1$ and —$SO_2$—$R^1$ and at the C-terminal end Y chosen from OH, $OR^1$, $NH_2$, $NHR^1$ or $NR^1R^2$, $R^1$ and $R^2$ being, independently of one another, chosen from a alkyl, aryl, aralkyl, alkylaryl, alkoxy and aryloxy group, which may be linear, branched, cyclic, polycyclic, unsaturated, hydroxylated, carbonylated, phosphorylated and/or sulfurized, said group possibly possessing in its backbone a heteroatom particularly 0, S and/or or N, and Pro* corresponding to Proline, an analogue or derivative thereof; comprising, for example, Myr-PPL-OH and Myr-PPR-OH.

Here can further be cited also the propigmenting and/or pro-mec dipeptides and tripeptides of general Formula X-($Xaa_1$)n-Pro*-$Xaa_2$-Y disclosed in WO2014/080376, with n=0, 1 or 2, $Xaa_1$ an hydrophobic aminoacid selected from Ala, Val, Met, Leu, Iso, Phe, Pro, and analogs and derivatives thereof; or a polar aminoacid selected from Ser, Thr, Tyr, Asp, Glu and analogs and derivatives thereof; and when n=2 the two aminoacids $Xaa_1$ being the same or different; $Xaa_2$ being an hydrophobic aminoacid selected from Ala, Val, Met, Leu, Iso, Phe, and analogs and derivatives thereof, or a basic aminoacid selected from Arg, Lys, His, and analogs and derivatives thereof; at the N terminal end X being selected from H, —CO—$R_1$ and —$SO_2$—$R_1$; at the C terminal end Y being selected from OH, $OR_1$, $NH_2$, $NHR_1$ or $NR_1R_2$; $R_1$ and $R_2$ being, independently from each other, selected from an alkyl, aryl, aralkyl, alkylaryl, alkoxy et aryloxy group, that can be linear, branched, cyclic polycyclic, saturated, unsaturated, hydroxylated, carbonylated, phosphorylated and/or sulfured, said group having or not an O, S and/or N heteroatom in its skeleton and Pro* corresponding to a Proline, analog or derivative thereof; comprising for example the following peptides Pal-SPR-OH, Pal-PPR-OH, Pal-QPA-OH, Pal-LPAOH, Myr-SPA-OH, Pal-PM-OH, Pal-PA-OH and Pal-PP-OH.

Suitable tetrapeptide derivatives for use as additional peptides according to the present invention include, but are not limited to, Pal-KTFK (SEQ ID NO: 5) or Ela-KTFK (SEQ ID NO: 14), Ela-KTAK (SEQ ID NO: 15), Ela-KAYK (SEQ ID NO: 16) or Ela-KFYK (SEQ ID NO: 17). Suitable pentapeptide derivatives for use as additional peptides herein include, but are not limited to, Pal-KTTKS (SEQ ID NO: 3) (available as Matrixyl® from Sederma), Pal-YGGFXaa (SEQ ID NO: 18) with Xaa being Leu or Pro, or mixtures thereof.

Suitable hexapeptide derivatives for use herein include, but are not limited to, Pal-VGVAPG (SEQ ID NO: 4), Pal-GKTTKS (SEQ ID NO: 19), Pal-HLDIIXaa with Xaa being Trp, Phe, Tyr, Tic, 7-hydroxy-Tic ou Tpi (SEQ ID NO: 20) and derivatives thereof. The mixture of Pal-GHK and Pal-GQPR (SEQ ID NO: 2) (Matrixyl® 3000, Sederma) can also be mentioned.

The following marketed peptides can be mentioned as well as additional active ingredients:

Vialox™ (INCI name=Pentapeptide-3 (synthetic peptide comprising alanine, arginine, isoleucine, glycine and proline)), Syn-ake™ (β-Ala-Pro-Dab-NH-Bzl) or Syn-Coll™ (Pal-Lys-Val-Lys-OH) marketed by Pentapharm;

Argireline™ (Ac-Glu-Glu-Met-Gln-Arg-Arg-$NH_2$ (INCI name=Acetyl hexapeptide-3) (SEQ ID NO: 21), Leuphasyl™ (Tyr-D-Ala-Gly-Phe-Leu) (SEQ ID NO: 22), Aldenine™ (Gly-His-Lys), Trylagen™ (INCI name=Pseudoalteromonas Ferment Extract, Hydro lyzed Wheat Protein, Hydro lyzed Soy Protein, Tripeptide-10 Citrulline (reaction product of Citrulline and Tripeptide-10 (synthetic peptide constituted of aspartic acid, isoleucine and lysine)), Tripeptide-1), Eyeseryl™ (Ac-β-Ala-His-Ser-His)(SEQ ID NO: 23), Serilesine™ (Ser-Ile-Lys-Val-Ala-Val) (SEQ ID NO 24) or Decorinyl™ (INCI name: Tripeptide-10 Citrulline=reaction product of Citrulline and Tripeptide-10 (synthetic peptide constituted of aspartic acid, isoleucine and lysine) marketed by Lipotec;

Collaxyl™ (Gly-Pro-Gln-Gly-Pro-Gln (SEQ ID NO 25)) or Quintescine™ (Cys-Gly) marketed by Vincience;

Cytokinol™ LS (casein hydrolysate) marketed by Les Laboratoires Serobiologiques/Cognis;

Kollaren™ (Gly-His-Lys), IP2000™ (Pal-Val-Tyr-Val) or Meliprene™ (INCI name=Monofluoroheptapeptide-1: reaction product of acetic acide and a synthetic peptide comprising arginine, glycine, glutamic acid, histidine, norleucine, p-fluorophenylalanine and tryptophan) marketed by l'lnstitut Européen de Biologie Cellulaire;

Neutrazen™ (Pal-His-D-Phe-Arg-$NH_2$) marketed by Innovations; or

BONT-L-Peptide™ (INCI name=Palmitoyl Hexapeptide-19: reaction product of palmitic acid and Hexapeptide-19 (synthetic peptide constituted of asparagine, aspartic acid, lysine and methionine), Timp-Peptide™ (INCI name=Acetyl Hexapeptide-20: reaction product obtained by acetylation of Hexapeptide-20 (synthetic peptide constituted of alanine, glycine, lysine, valine and proline) or ECM Moduline™ (INCI name=Palmitoyl Tripeptide-28: reaction product of palmitic acid and Tripeptide-28 (synthetic peptide constituted of arginine, lysine and phenylalanine) marketed by lnfinitec Activos.

It is also possible to envisage combining the plant cells according to the invention with one or more cyclic peptides, in particular those extracted from linseed oil described in the Applicant's patent application FR1850845.

Different compositions/formulations according to the invention are described below with some examples of additional active ingredients.

A composition according to the invention forming a concentrated active ingredient according to the invention is as described in point A/ above.

This ingredient is generally formulated within a range of 0.1% to 20%, preferably between 1 to 10%, more preferably between 2% and 5%.

1) Day Cream

TABLE 16

| Raw materials | INCI name | % |
|---|---|---|
| Part A: | | |
| HO | Aqua | qsp100 |
| Carbopol ™ Ultrez 10 | Carbomer | 0.30 |

TABLE 16-continued

| Raw materials | INCI name | % |
|---|---|---|
| Part B: | | |
| Glycerin | Glycerin | 2.50 |
| Octanediol | Caprylyl Glycol | 0.50 |
| Part C: | | |
| Natrosol 250M | Hydroxyethylcellulose | 0.20 |
| Phenoxyethanol | Phenoxyethanol | qs |
| Part D: | | |
| Crodamol CSO | Cetearyl Ethylhexanoate | 6.00 |
| Pemulen TR2 | Acrylates/C 10-30 Alkyl Acrylate Crosspolymer | 0.20 |
| Part E: | | |
| Potassium sorbate | Potassium Sorbate | qs |
| Part F: | | |
| Tween 20 | Polysorbate 20 | 0.50 |
| NaOH 30% | Sodium Hydroxide | 0.40 |
| Part G: | | |
| Demineralised water | Aqua | 5.00 |
| NaOH 30% | Sodium Hydroxide | 0.40 |
| Part H: | | |
| Ingredient according to the invention | / | 2.00 |

2) Night Cream

TABLE 17

| Raw materials | INCI name | % |
|---|---|---|
| Part A: | | |
| $H_2O$ | Aqua | qsp100 |
| Carbopol Ultrez 10 ™ | Carbomer | 0.30 |
| Part B: | | |
| Brij S2-SS-(RB) ™ | Steareth-2 | 5.00 |
| Brij SIO-SO-(RB) ™ | Steareth-10 | 0.40 |
| Crodafos CES-PA-(RB) ™ | Cetearyl Alcohol (and) Dicetyl Phosphate (and) Ceteth-10 Phosphate | 1.20 |
| Crodacol CS90-PA-(RB) ™ | Cetearyl Alcohol | 4.00 |
| Crodamol AB-LQ-(RB) ™ | C12-15 Alkyl Benzoate | 1.50 |
| Crodamol OSU-LQ-(JP) ™ | Diethylhexyl Succinate | 7.00 |
| Part C: | | |
| Glycerin | Glycerin | 2.50 |
| Octanediol | Caprylyl Glycol | 0.50 |
| Part D: | | |
| Phenoxyethanol | Phenoxyethanol | qs |
| Part E: | | |
| Potassium sorbate | Potassium sorbate | qs |
| Part F: | | |
| $H_2O$ | Aqua | 4.00 |
| NaOH 30 % | Sodium Hydroxide | 0.40 |
| Part G: | | |
| Ingredient according to the invention | / | 2.00 |

Example(s) of Additional Ingredient(s):

A calming ingredient for sensitive skin such as:

PACIFEEL™, marketed by Sederma, comprising an extract of *Mirabilis Jalapa.*

An hydrating ingredient such as:

AQUALANCE™, marketed by Sederma, hydrating active, osmoprotector composed of homarin and erythritol.

REVIDRAT™, marketed by Sederma, which in particular improves the cohesion of the epidermis and its hydration.

An ingredient that acts on the radiance of the complexion such as:

EVERMAT™, marketed by Sederma, comprising a combination of an extract of *Enantia chlorantha* rich in protoberberins and oleanolic acid; decreases pore size and shine; refines the texture of acne-prone skin.

A moisturizing/smoothing ingredient such as:

OPTIM HYAL™, marketed by Sederma, contains oligosaccharides of acetylated glucuronic acid having a structure similar to fragments of hyaluronic acid.

A sebum-regulating ingredient such as:

SEBULESS™, marketed by Sederma, comprising an extract of *Syringa vulgaris* obtained by in vitro cell culture, purifying sebo-regulator, mattifies and refreshes the complexion, blurs imperfections.

PORETECT™, marketed by Sederma, comprising a combination of extracts of flax seeds and celery titrated in cylolinopeptides and senkyunolides, which brings firmness, tone and density to the skin, thus strengthening the structures of maintenance of the pores which collapse with age.

An ingredient acting on the elastic properties of the skin/skin barrier such as:

IDEALIFT™, marketed by Sederma, comprising the lipodipeptide N-acetyl-Tyrosyl-Arginyl-O-hexadecyl ester, combating facial flaccidity and improving resistance to gravity, in particular through the stimulation of elastin.

DERMAXYL™, marketed by Sederma, combining ceramide 2, cement of the stratum corneum, and a palmitoylated matrikine Pal-Val-Gly-Val-Ala-Pro-Gly, which smooths wrinkles and repairs the skin barrier.

An anti-fatigue ingredient like:

PRODIZIA™, marketed by Sederma, containing an extract of *Albizia julibrissin*, which promotes the visible reduction of the signs of fatigue: dark circles, under eye bags, dull complexion and drawn lines by repairing and protecting the skin from damage caused by glycation.

An anti-pollution ingredient such as:

CITYSTEM™, marketed by Sederma, based on plant cells obtained in vitro from *Marrubium vulgare* with a high concentration of Forsythoside B; used against pollution attacks: makes the skin soft and smooth, refines the skin texture, reduces the visibility of comedones, leaving the skin radiant and purified.

E/ In-Vivo Studies

General Principles

The evaluation of the efficacy of the composition according to the invention was carried out on 27 volunteers. Since it is not possible to expose volunteers to blue light for hours, panelists with special characteristics were selected. For all these studies, the volunteers had to have significant daily contact with the screens, to experience some fatigue and that this fatigue was visible on the face. In particular, they could have a dull complexion and/or imperfections and/or "tired/crumpled", dehydrated facial skin, with a loss of tone and radiance.

The study of the invention composition benefit was carried out in the following areas: hydration, smoothing, radiance, skin tone and cutaneous fatigue.

The study was done on the face for 8 weeks (measured at TO and T8 weeks).

In the study, the volunteers applied to one side of the face a day cream in the morning and a night cream in the evening (formulations of galenic part D above). On the other side of the face, a placebo day cream as well as a night cream (same formulas without active) were applied in a similar way. The volunteers did not know which creams corresponded to the invention.

Statistical studies were performed using Student's t test or, if necessary, with a nonparametric Wilcoxon test. Bilateral tests were performed on paired series.

1/ Hydration

Method

An innovative device, Epsilon™, was used for this study. It has the particularity of providing not a value but an image of hydration. This device is derived from the Skinchip™ technology. The device is fitted with a sensor, comprising 76,800 pixels, which measures up to 50 μm in depth. Each pixel gives a value ε of dielectric permittivity of the skin, a parameter which changes from 0 to 85 (air=1 and water=80). The measurement provides an image allowing to visually assess the effect of the products tested on skin topography, and by extension its homogeneity or even its suppleness because hydration improves this parameter.

Results

Variation in skin hydration; effect of the cream according to the invention (N=27)

TABLE 18

| | Cream according to the invention | | Placebo cream | |
|---|---|---|---|---|
| Hydratation (permittivity ε) | T0 | T8 weeks | T0 | T8 weeks |
| % variation vs. TO | | +13.8% | | −2.1% |
| Significance | | p < 0.05 | | nsd |
| % of improvement of the cream according to the invention vs. the placebo cream | +15.9% (p < 0.01) | | | |

After 2 months of application of the cream according to the invention, the skin is more hydrated compared to the placebo (p<0.01). The latter does not bring any significant benefit.

2/ Skin Smoothing

Method

For this type of evaluation, the Epsilon™ which can also provide information on the smoothing aspect was used. The image negative obtained for the hydration gives this type of information. Fewer pixels in the image indicate a smoothing effect.

Results

Variation in the relief of the skin (more or less smooth appearance); effect of a cream according to the invention (N=27)

TABLE 19

| | Cream according to the invention | | Placebo cream | |
|---|---|---|---|---|
| Relief (number of pixels) | T0 | T8 weeks | T0 | T8 weeks |
| % variation vs. TO | | −7.5% | | −2% |
| Significance | | $p < 0.05$ | | nsd |
| % of improvement of the cream according to the invention vs. the placebo cream | −5.5% | ($p < 0.05$) | | |

The results of these two studies show a marked improvement in skin smoothing. With the cream according to the invention, the smoothing is markedly improved by 5.5% compared with the placebo ($p<0.05$). This percentage clearly indicates an improvement on skins that are relatively young and slightly marked.

3/ Cutaneous Radiance

Method

This study was conducted using the C-Cube™ color camera (Pixience) which uses constant diffused LED illumination with polarization to avoid shininess. The images are self-calibrated and homogenized. Structures smaller than 20 μm can be seen with a zoom. An algorithm combining colorimetric measurements and analysis of variance provides a radiance index that is correlated with the clinical grading method CLCT (Color Luminosity Brightness Transparency). This index has a physiological window established, during the study, between 35 and 70 units. The deltas measured after application are expressed as a % of this physiological scale of 35 units.

Results

Variation of the radiance of the skin; effect of a cream according to the invention (N=25)

TABLE 20

| | Cream according to the invention | | Placebo cream | |
|---|---|---|---|---|
| Radiance index | T0 | T8 weeks | T0 | T8 weeks |
| % variation vs. T0 | | +4.4% | | −2.7% |
| Significance | | $p < 0.09$ | | nsd |
| % of improvement of the cream according to the invention vs. the placebo cream | +7.1% | ($p < 0.05$) | | |

It is noted that skin radiance is improved after application of the invention cream, radiance being increased by +4.4% at a time when the placebo site has deteriorated on average by −2.7%. The difference is significantly in favor of the invention cream compared to the placebo cream ($p<0.05$).

4/ Skin Tone and Fatigue

Method

The Cutometer® MPA580 (C&K) is conventionally used to study the effects of cosmetic products on the viscoelastic parameters of the skin. It measures the deformation of a skin area subjected to mechanical suction stress and its power of recovery. The possibility of applying several successive deformations was used because it allows to measure the "fatigability" of the skin over time. The evaluation of the extensibility (Uf) provides an indication of its tone/firmness. An internal study on 62 volunteers, aged 23 to 81 years, made it possible to establish a correlation with age for the skin fatigue parameter and thus to provide a theoretical gain in age.

Results

Variation in cutaneous fatigue and tone; effect of a cream according to the invention (N=27)

TABLE 21

| | Cream according to the invention | | Placebo cream | |
|---|---|---|---|---|
| Cutaneous fatigue R4_R1 (in mm) | T0 | T8 weeks | T0 | T8 weekss |
| % variation vs. T0 | | −7.9% | | +4.2% |
| Significance | | $p < 0.05$ | | nsd |
| % of improvement of the cream according to the invention vs. the placebo cream | −12.1% | ($p < 0.05$) | | |

TABLE 22

| | Cream according to the invention | | Placebo cream | |
|---|---|---|---|---|
| Skin stretch Uf (in mm) | T0 | T8 weeks | T0 | T8 semaines |
| % variation vs. T0 | | −4.1% | | +1.5% |
| Significance | | $p < 0.05$ | | nsd |
| % of improvement of the cream according to the invention vs. the placebo cream | −5,6% | ($p < 0,05$) | | |

This table shows that the application of the invention composition can "relax" the skin by making it significantly less stretchy, one of the signs of aging, by 5.6%, and significantly decreases its "fatigability" at repeated tractions of about 12%.

All of these in vitro and in vivo results confirm the undoubted interest of a composition according to the invention for a cosmetic or dermatological treatment.

The invention claimed is:

1. A cosmetic or dermatological composition consisting of:

chrysin;

rosmarinic acid;

at least one peptide or derivative thereof, having a sequence of 4 to 10 amino acids comprising the active sequence GQPR (SEQ ID NO 1); and a physiologically acceptable medium, wherein for the at least one derivative thereof:

an acyl (—CO-$R^1$), a sulfonyl (—$SO_2$-$R^1$) or a biotinoyl group is present at the N-terminal end; and/or $OR^1$, $NH_2$, $NHR^1$ or $NR^1R^2$ is present at the C-terminal end, $R^1$ and $R^2$ being, independently of one another, chosen from an alkyl, aryl, aralkyl, alkylaryl, alkoxy, saccharide and aryloxy group, where the alkyl group contains 1 to 24 carbon atoms and includes linear, branched, cyclic, polycyclic and unsaturated alkyls, and where the carbon atoms may be substituted with hydroxyl, carbonyl, a sulfur-containing group or phosphorylated, and the alkyl group may have in its backbone one or more O, S and/or N heteroatoms.

2. The composition according to claim 1, wherein the chrysin is present at a concentration ranging from 0.2 to 20,000 ppm in weight with regard to the total weight of the composition.

3. The composition according to claim 1, wherein the rosmarinic acid is present at a concentration ranging from 0.1 to 10,000 ppm in weight with regard to the total weight of the composition.

4. The composition according to claim 1, wherein the at least one peptide or derivative thereof is present at a concentration ranging from 0.5 to 50,000 ppm in weight with regard to the total weight of the composition.

5. The composition according to claim 1, wherein the rosmarinic acid is present in the form of a plant extract.

6. The composition according to claim 5, wherein the plant is chosen among rosemary (*Rosmarinus officinalis*), lemongrass, sages, basil, mints, perilla, brunelle, orthosiphon, lavenders, comfrey, savory, horehound, hyssop, monarda, plants of the Labiee, Boraginaceae and Apiaceae families.

7. The composition according to claim 1, wherein $R^1$ and/or $R^2$ corresponds to an alkyl chain of 3 to 24 carbon atoms.

8. The composition according to claim 1, wherein the at least one peptide or derivative thereof comprises only one modification in the N-terminal position corresponding to an acyl group —CO-$R^1$.

9. The composition according to claim 1, wherein the acyl group —CO—$R_1$ is chosen among an octanoyl ($C_8$), decanoyl ($C_{10}$), lauroyl ($C_{12}$), myristoyl ($C_{14}$), palmitoyl ($C_{16}$), stearoyl ($C_{18}$), biotinoyl, elaidoyl, oleoyl and lipoyl.

10. The composition according to claim 1, wherein the at least one peptide or derivative thereof comprises 4 amino acids corresponding to the GQPR sequence (SEQ ID NO 1).

11. The composition according to claim 1, wherein the composition comprises the peptide derivative Pal-GQPR (SEQ ID NO 2).

12. The composition according to claim 1, consisting of chrysin, rosmarinic acid, Pal-GQPR-OH (SEQ ID NO 2) and the physiologically acceptable medium.

13. A method for a non-therapeutic cosmetic treatment of skin or its appendages, comprising contacting the skin or its appendages with the composition according to claim 1.

14. The method according to claim 13, for treating the effects of photoaging.

15. The method according to claim 13, for an antioxidant treatment.

16. The method according to claim 13, for treating the harmful effects of blue light and/or to increase its beneficial effects.

17. The method according to claim 13, to improve hydration, smoothness, radiance and/or tone of skin.

18. The method according to claim 13, wherein the treatment is topical.

19. A topical medical treatment of skin or its appendages that includes contacting the skin or its appendages with the composition according to claim 1.

* * * * *